United States Patent [19]

Suzuki

[11] Patent Number: 4,565,700

[45] Date of Patent: Jan. 21, 1986

[54] PROCESS FOR PREPARATION OF SUBSTANCE HAVING HYPOTENSIVE COMPONENT

[76] Inventor: Tetsuya Suzuki, 3-1, Teraodai 2-chome, Ayase-shi, Kanagawa 252, Japan

[21] Appl. No.: 560,158

[22] Filed: Dec. 12, 1983

[30] Foreign Application Priority Data

Apr. 16, 1982 [JP] Japan .................................. 57-62483
Apr. 14, 1983 [WO] PCT Int'l Appl. ... PCT/JP83/00116

[51] Int. Cl.$^4$ ............................................. A61K 35/78
[52] U.S. Cl. ................................................. 424/195.1
[58] Field of Search ........................................ 424/195

[56] References Cited

PUBLICATIONS

Chem. Abst. 54: 19956b, 1960.
Chem. Abst. 55: 14702c, 1961.
Chem. Abst. 55: 17888c, 1961.

*Primary Examiner*—Allen J. Robinson
*Assistant Examiner*—John W. Rollins, Jr.
*Attorney, Agent, or Firm*—Sherman and Shalloway

[57] ABSTRACT

Disclosed is a process for the preparation of a substance having a hypotensive component, which comprises mixing and extracting an oil-squeezed component from a soybean oil-preparing step with water, an aqueous solution of an acid, an aqueous solution of a salt or an aqueous solution of an acid and a salt, subjecting the extract to centrifugal separation, separating a hypotensive component from the aqueous phase, and, if necessary, drying the separated hypotensive component. This substance is valuable as a medicine or in the field of health-promoting foods.

17 Claims, 4 Drawing Figures

PROCESS FOR PREPARATION OF SUBSTANCE HAVING HYPOTENSIVE COMPONENT

DESCRIPTION

1. Technical Field

The present invention relates to a process for preparing a substance having a valuable hypotensive action (hereinafter referred to as "effective component") at the step of preparing an oil from soybeans.

2. Technical Background

F. G. Valdecasas et al. have already published in three reports that soybeans contain a component valuable as a hypotensive agent [Med., Exp. 2, 3–36, Exp. 3, 272–278 and Exp. 3, 289–296 (1960)]. However, a process for obtaining this effective component is important from the practical viewpoint. The inventor had made research with a view to developing such a process, and as the result, the inventor has now completed the present invention.

SUMMARY OF THE INVENTION

The gist of the present invention resides in a process for the preparation of a substance having a hypotensive component, which comprises mixing an oil component squeezed or extracted from from a soybean with water, an aqueous solution of an acid, an aqueous solution of a salt or an aqueous solution of an acid and a salt, subjecting the extract to centrifugal separation, separating a hypotensive component from the aqueous phase and, if necessary, drying the separated hypotensive component.

DETAILED DESCRIPTION OF THE INVENTION

The present invention will now be described in detail. As the starting soybean component to be extracted with water or an aqueous solution, there can be mentioned a miscella obtained by solvent extraction of soybeans, a 95% crude oil obtained by separating the extracting solvent from the miscella, a crude oil obtained by further removing the solvent by a stripper, a gum formed by adding water or an acidic aqueous solution to the crude oil and a degummed oil obtained by removing this gum. At any rate, when an oil, other than degummed oil or a gum is used as the soybean component subject to the extraction step, the gum is precipitated in the emulsified state in the extracting aqueous solution. Accordingly, in this case, in order to increase the recovery ratio of the effective component, it is preferred that the gum having a surface active function be deactivated and coagulated.

The amount of water to be used is at least 5%, preferably 20 to 30%, based on the soybean component to be extracted. Water may be used for the extraction, but an aqueous solution of ammonium sulfate, sodium chloride or calcium carbonate is preferably used. The concentration may be increased to the saturation concentration, but the concentration is preferably 0.1 to 3%. An acid designated as a food additive, especially an organic acid, e.g. lactic acid, acetic acid, succinic acid, oxalic acid, malic acid, citric acid, etc., may be added to water or the aqueous salt solution in an amount of up to 10%. The mixing extraction temperature is lower than 100° C., preferably lower than 90° C., and the temperature is lowered below 50° C. as promptly as possible to prevent deactivation of the effective component. The oil and gum are separated from the aqueous solution by a centrifugal separator. If this extracting operation is repeated, the yield is increased. The effective component is separated from the so-obtained aqueous solution.

The following methods can be adopted for this separation. The first method is the salting-out method in which the effective component is precipitated at a temperature lower than 50° C. by adding ammonium sulfate or sodium chloride so that the salt concentration is higher than 10%. The second method is the concentration method in which a concentration device having a short heating residence time (for example, 5 minutes or shorter) such as a flash evaporator or a wet wall type evaporator, is used, and the solution is concentrated by more than 90% under atmospheric or reduced pressure and the concentrate is cooled below 40° C. as promptly as possible, whereby the effective component is precipitated. Furthermore, there may be adopted a method in which the aqueous solution is concentrated to the economical limit (the concentration is increased by about 3 times) by using a reverse osmosis membrane where no heating is necessary, and the effective component is precipitated by the first salt-out method or the second evaporation method.

The precipitated product is recovered by filtration at normal, i.e. room, temperature. The filtrate may be circulated to the concentration step and used again. If necessary, the effective component is recrystallized from an aqueous solution of methanol or ethanol having a concentration of at least 60%, preferably 75 to 90%. In this case, in order to prevent deactivation of the effective component, it is preferred that the concentration be carried out as soon as possible. Namely, the concentration is carried out under temperature-time conditions included within the operation region A in the temperature-time curve of FIG. 4. If the operation is carried out under conditions included within the region B, good results are not obtained. The effective component is dried in a reduced pressure drier under the temperature-time conditions included within the region A in FIG. 4, preferably at a temperature lower than 45° C. within the region A.

When the obtained substance is analyzed by the thin layer chromatography, it is considered that the substance may probably be a polysaccharide nucleic acid, but the details of the structure are unknown.

The effective component obtained according to the present invention has apparently the function of reducing the blood pressure in rats, and the time of the duration of the hypotensive effect is relatively long.

It has thus been clarified that a soybean oil, especially a soybean milk, contains a component having a hypotensive action in addition to the known effective components such as a linoleic acid component having a cholesterol-removing action and a vitamin E component having an arterial sclerosis-preventing action, and the effective component obtained according to the present invention is valuable not only as a medicine but also in the field of health-promoting foods.

Figure 1:
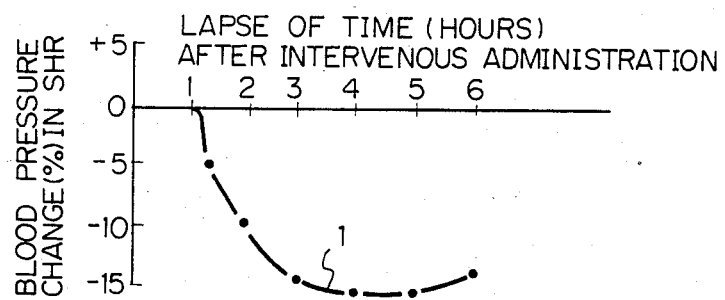
FIGS. 1 through 3 are diagrams illustrating the change of the blood pressure with the lapse of time, which is observed when the effective component obtained according to the present invention is administered.

In the drawings, 1, 2, 3, 4, 5, 6 and 7 are curves showing the changes of the blood pressure with the lapse of time, observed in Examples 1, 2, 3, 4, 5, 6, and Comparative Example, respectively.

BEST MODES FOR CARRYING OUT THE INVENTION

The process for the preparation of the effective component of the present invention and the hypotensive action thereof will now be described with reference to the following Examples that by no means limit the scope of the invention. In the Examples, all of "parts" and "%" are by weight unless otherwise indicated. The pharmacological test was carried out according to the following procedures.

A sample obtained in each Example was dissolved in a physiological saline solution and administered to an unanesthetized, spontaneous hypertensive rat (SHR) intravenously at a dose of 10 mg/kg or orally at a dose of 0.5 g/kg. The change of the blood pressure was directly measured by the surgical method during a period of 6 hours after the administration and the ratio (%) of the change was determined.

EXAMPLE 1

To 5 kg of a crude soybean oil was added 1 liter of a 3% aqueous solution of ammonium sulfate, and the mixture was stirred at 50° C. for 5 minutes and was separated by a centrifugal separator to obtain 600 cc of an aqueous layer. Then, 300 g of ammonium sulfate was added to the aqueous layer and the mixture was stirred at room temperature to precipitate a solid. The solid was recovered by filtration, washed with a small amount of water and vacuum-dried at a temperature lower than 40° C. The obtained solid had a light brown color and the amount obtained of the solid was 1.7 g. The results of the animal test of the product are shown in FIG. 1.

In FIG. 1, the blood pressure change (%) of SHR is plotted on the ordinate and the lapse of time (hours) after the administration is plotted on the abscissa. As is apparent from Curve 1 in FIG. 1, the blood pressure was reduced within a short time after the administration.

EXAMPLE 2

Figure 2:
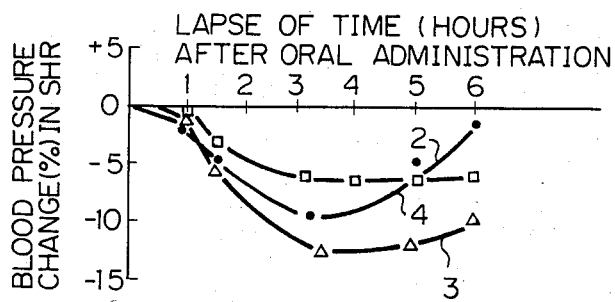

To 6 kg of miscella obtained by extraction of soybean oil was added 2 l of a 2% aqueous solution of acetic acid, and the mixture was stirred at 60° C. for 10 minutes and 1.8 l of an aqueous layer (1) was separated. Then, 1 l of 2% acetic acid was added to the residual miscella and the mixture was stirred at room temperature, and 0.7 l of an aqueous layer (2) was separated. The aqueous layers (1) and (2) were combined and the mixture was concentrated at a temperature lower than 60° C. by a flash evaporator (the residence time was shorter than 5 minutes) so that the volume was reduced to 1/5. Then, ammonium sulfate was added to the concentrate at room temperature in an amount of 200 g per 0.5 l of the concentrate to effect salting-out. The precipitate was recovered by filtration and vacuum-dried at a temperature lower than 40° C. to obtain 1.5 g of a product having a light yellowish brown color. The results of the animal test are shown in Curve 2 of FIG. 2.

EXAMPLE 3

To 5 kg of a degummed oil from extracted soybean oil was added 7.50 cc of a 2% aqueous solution of lactic acid, and the mixture was stirred at 40° C. for 10 minutes. The aqueous layer was separated and concentrated at 70° C. by a flash evaporator, and the concentrate was subjected to evaporation to dryness. Then, the solid was extracted two times with 50 cc of a 75% aqueous solution of ethanol, and the extract was recovered by filtration and concentrated by a flash evaporator so that the volume was reduced to 1/10. The concentrate was dried at a temperature lower than 40° C. by a vacuum drier to obtain 0.54 g of a solid having a light yellowish brown color. The results of the animal test are shown in Curve 3 of FIG. 2.

EXAMPLE 4

To 7 kg of a gum obtained from extracted soybean oil was added 1 liter of a mixture of a 2% aqueous solution of sodium chloride and a 2% aqueous solution of succinic acid, and the mixture was stirred at 70° C. for 10 minutes and subjected to centrifugal separation. Then, 500 cc of a 2% aqueous solution of sodium chloride was added to the separated gum, and the above-mentioned stirring and separation operations were repeated. The obtained aqueous layers were combined, and the mixture was concentrated by a reverse osmosis membrane device so that the volume reduced to 1/3. Then, 200 g of sodium chloride was added to the concentrate to effect concentration. The solid was recovered by filtration, washed with a small amount of water and vacuum-dried at a temperature lower than 40° C. to obtain 21.5 g of a solid having a light brown color. The results of the animal test are shown in Curve 4 of FIG. 2.

EXAMPLE 5

Figure 3:
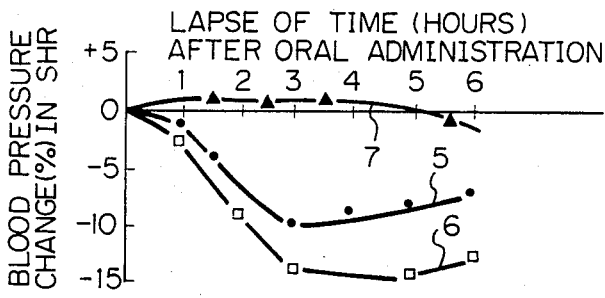

To 5.5 g of a degummed oil obtained from soybean oil was added 600 cc of a 1% aqueous solution of succinic acid, and the mixture was stirred at 50° C. for 5 minutes and the aqueous layer was separated. Then, 180 g of ammonium sulfate was added to the aqueous layer and the mixture was stirred. The precipitated solid was recovered by filtration, washed with a small amount of water and vacuum-dried at a temperature lower than 40° C. to obtain 0.44 g of a solid having a light brown color. The results of the animal test are shown in Curve 5 of FIG. 3.

EXAMPLE 6

To 5.4 kg of a crude oil obtained by extraction of soybean oil was added 3 l of an aqueous solution containing 1% of ammonium sulfate and 1% of oxalic acid, and the mixture was stirred at an initial temperature of 70° C. for 5 minutes and separated by a centrifugal separator to obtain 1560 cc of an aqueous layer. The aqueous layer was concentrated by a reverse osmosis membrane so that the volume was reduced to 1/3. Then, the concentrate was treated at 60° C. by a flash evaporator so that the volume was reduced to 1/10. The precipitated solid was recovered by filtration and was refined by a 90% aqueous solution of methanol in the same manner as described in Example 3. A solid having a light yellowish brown color was obtained in an amount of 5.1 g. The results of the animal test are shown in Curve 6 of FIG. 3.

COMPARATIVE EXAMPLE

Figure 4:
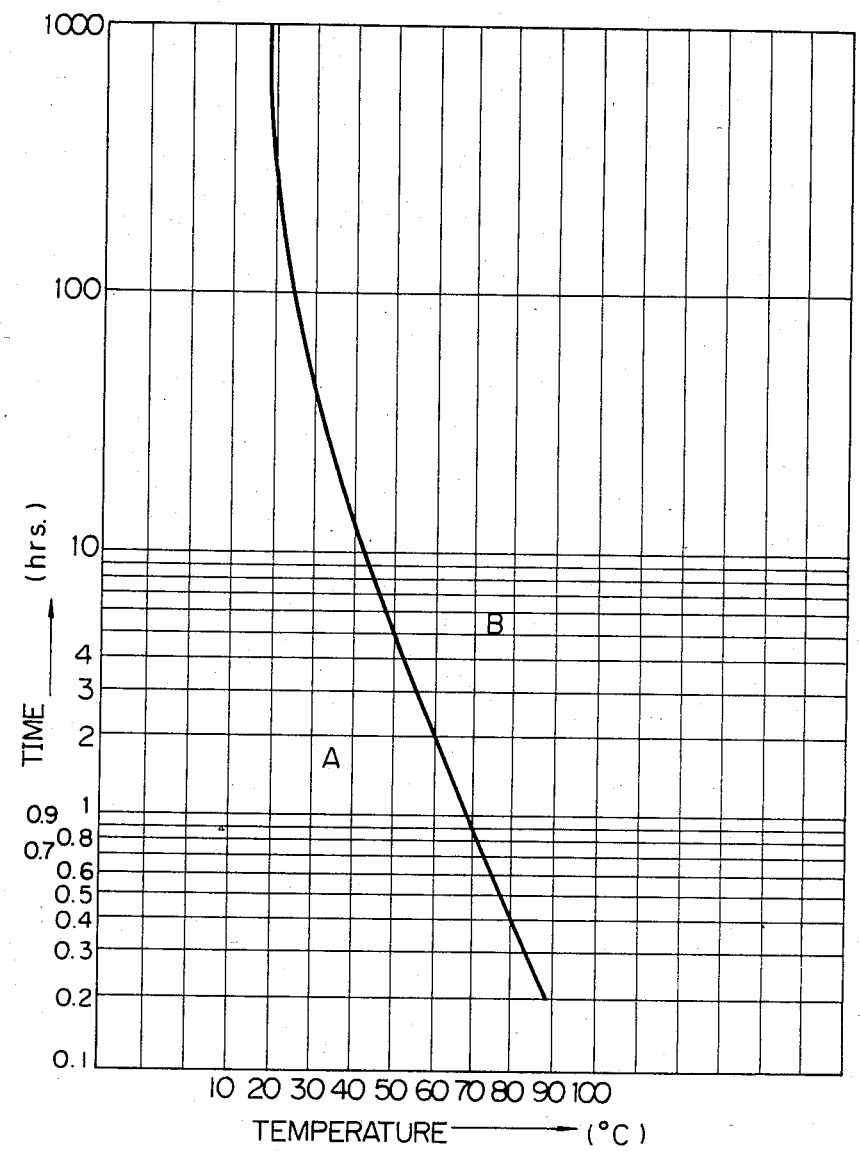
FIG. 4 is a diagram illustrating temperature-time conditions in the treatment in the process of the present invention.

The procedures of Example 3 were repeated in the same manner as described in Example 3 except that the concentration was carried out batchwise at an inner temperature of 70° to 75° C. for 4 hours (the temperature-time conditions were included within the region B in FIG. 4). The results of the animal test are shown in Curve 7 of FIG. 3.

INDUSTRIAL UTILIZABILITY

According to the process of the present invention, a substance having a hypotensive component having a durable hypotensive action can be obtained from the step of preparing a soybean oil, and this substance is valuable as a hypotensive agent in the field of medicines or health-promoting foods.

I claim:

1. A process for the preparation of a substance having a hypotensive component, which comprises (i) mixing an oil component squeezed or extracted from a soybean, with an aqueous extraction medium composed of (A) water, (B) an aqueous solution containing a salt selected from the group consisting of ammonium sulfate and sodium chloride in the concentration of 0.1 to 3%, (C) an aqueous solution containing an acid selected from the group consisting of lactic acid, acetic acid, succinic acid, oxalic acid, malic acid and citric acid in the concentration of up to 10% or (D) a combined aqueous solution of (B) and (C), said extraction medium being used in an amount of at least 5% based on the oil component, at such a temperature that the temperature of the mixture is lower than 90° C. at the initial stage but is lowered below 50° C. at the final stage, thereby to extract said substance in the aqueous extraction medium, (ii) subjecting the mixture to centrifugal separation to separate the aqueous extract from the oil phase, and (iii) recovering the substance in the solid state from the aqueous extract, said steps (i) and (ii) being carried out under temperature-time conditions included within the operation region A shown in FIG. 4.

2. A process for the preparation of a substance having a hypotensive component according to claim 1, wherein the oil component is a miscella, a solvent-removed oil (95%), a crude oil, a degummed oil or a gum.

3. A process for the preparation of the substance having a hypotensive component according to claim 2 wherein the oil component is a miscella.

4. A process for the preparation of the substance having a hypotensive component according to claim 2 wherein the oil component is a solvent-removed oil (95%).

5. A process for the preparation of the substance having a hypotensive component according to claim 2 wherein the oil component is a crude oil.

6. A process for the preparation of the substance having a hypotensive component according to claim 2 wherein the oil component is a degummed oil.

7. A process for the preparation of the substance having a hypotensive component according to claim 2 wherein the oil component is a gum.

8. A process for the preparation of a substance having a hypotensive component according to claim 1 wherein the step of recovering the substance having a hypotensive component in the solid state from the aqueous extract comprises concentrating the aqueous extract under temperature-time conditions such that the aqueous extract is not exposed to a temperature higher than 80° C. for any longer than 30 minutes.

9. A process for the preparation of a substance having a hypotensive component according to claim 8 wherein the concentration of the aqueous extract is carried out continuously.

10. A process for the preparation of a substance having a hypotensive component according to claim 1, wherein the separation of the hypotensive component is accomplished by salting-out.

11. A process for the preparation of a substance having a hypotensive component according to claim 10, wherein the salting-out is performed by using ammonium sulfate, sodium chloride or a mixture thereof.

12. A process for the preparation of a substance having a hypotensive component according to claim 1, wherein the separation of the hypotensive component is accomplished by concentration and salting-out in combination.

13. A process for the preparation of a substance having a hypotensive component according to claim 1, which further comprises drying the substance obtained in step (iii) under a reduced pressure under temperature-time conditions included with the operation region A shown in FIG. 4.

14. The process of claim 1 wherein the aqueous extraction medium is composed of (A) water.

15. The process of claim 1 wherein the aqueous extraction medium is composed of (B) the aqueous solution containing ammonium sulfate or sodium chloride.

16. The process of claim 1 wherein the aqueous extraction medium is composed of (C) the aqueous solution containing lactic acid, acetic acid, succinic acid, oxalic acid, malic acid or citric acid.

17. The process of claim 1 wherein the aqueous extraction medium is composed (D) the combined aqueous solution of (B) and (C).

* * * * *